United States Patent [19]

Imai

[11] 4,298,499
[45] Nov. 3, 1981

[54] RECOVERY OF CATALYSTS

[75] Inventor: Tamotsu Imai, Mt. Prospect, Ill.

[73] Assignee: UOP Inc., Des Plaines, Ill.

[21] Appl. No.: 167,947

[22] Filed: Jul. 14, 1980

[51] Int. Cl.³ .................. B01J 31/40; B01J 31/18; C07C 27/22; C01G 55/00

[52] U.S. Cl. .................. 252/414; 252/431 N; 423/22; 423/139; 568/909

[58] Field of Search .............. 252/414, 412; 568/909; 203/6, 72; 423/22, 139

[56] References Cited

U.S. PATENT DOCUMENTS

| | | | |
|---|---|---|---|
| 2,880,241 | 3/1959 | Hughes | 568/909 |
| 3,594,425 | 7/1971 | Brader, Jr. | 568/909 |
| 3,954,877 | 5/1976 | Gipson | 568/909 |
| 4,045,492 | 8/1977 | Kniese | 568/909 |
| 4,190,729 | 2/1980 | Forster | 203/6 |

*Primary Examiner*—P. E. Konopka
*Attorney, Agent, or Firm*—James R. Hoatson, Jr.; Raymond H. Nelson; William H. Page, II

[57] ABSTRACT

Metallic catalysts such as Group VIII metal complexes which are used in hydroformylation reaction for the production of alcohols from olefins will be found in the product mixture. The separation and recovery of these metal catalysts from the product mixture may be accomplished by treating said product mixture with a biphyllic ligand capable of forming a soluble complex with the metallic catalyst and thus can be removed from the desired product.

16 Claims, 1 Drawing Figure

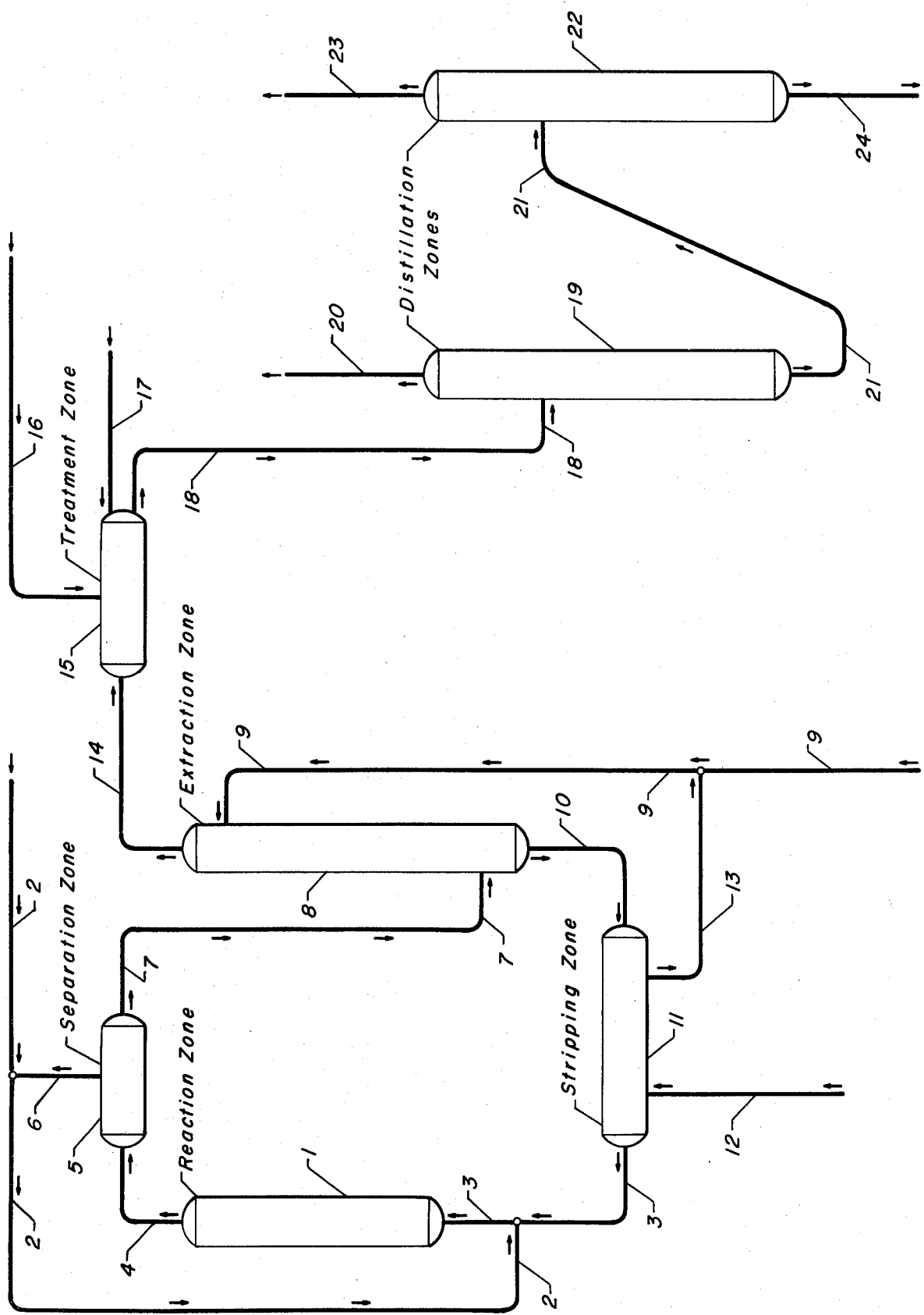

RECOVERY OF CATALYSTS

DESCRIPTION OF THE INVENTION

This invention relates to a process for the recovery of catalysts which have been used in hydroformylation processes. More specifically, the invention is concerned with a process for recovering metal catalysts such as Group VIII metal complexes which have been utilized to synthesize alcohols in a one-step hydroformylation reaction.

Alcohols are important basic chemicals which find a wide variety of uses in industry. For example, ethyl alcohol is a basic chemical which is used as a solvent and in the manufacture of intermediates, dyes, synthetic drugs, synthetic rubbers, detergents, cleaning source, surface coatings, cosmetics, pharmaceuticals, rocket fuel, beverages, etc. Isopropyl alcohol is used in the manufacture of acetone which in turn is a source of acetic anhydride, diacetone alcohol, methyl isobutyl ketone and other derivatives. It is also used as a solvent for essential oils, gums, resins; as a latent solvent for cellulose derivatives; as an anti-stalling agent in liquid fuels or as an intermediate in the manufacture of pharmaceuticals, perfumes, lacquers, rocket fuel, etc. Likewise, dodecyl alcohol which is also known as lauryl alcohol is used in the manufacture of synthetic detergents, lube additives, pharmaceuticals, rubber, textiles, and perfumes. Tetradecanol which is also known as myristyl alcohol is used in organic synthesis, as a plasticizer, antifoam agent, as a perfume fixative for soaps and cosmetics as well as other uses.

The prior art has shown, as exemplified by the Oxo process, that aldehydes may be produced from olefinic hydrocarbons by treatment with carbon monoxide and hydrogen using a cobalt carbonyl catalyst. It has further been shown in the prior art, as exemplified by U.S. Pat. No. 2,880,241, that rhodium is known to be a much more active catalyst than cobalt. The activity and selectivity of rhodium catalysts may be altered by modifying the catalyst with other compounds such as tertiary amines. For example, when using tertiary amines to modify rhodium catalysts, it is possible to produce alcohols rather than aldehydes in this process.

The commercialization of processes for the synthesis of alcohols utilizing rhodium complex catalysts is affected by the difficulty which is attendant in the recovery of rhodium, a particular disadvantage which negates the commercial use of such catalyst complexes comprising the frequency losses of the precious metal which may occur under process conditions, the loss of only a trace amount of this precious metal making the process uneconomical to operate and overshadowing the attractive conversion rate and selectivity which is obtained when using this metal. The separation of the rhodium catalyst from alcohol products, especially high molecular weight alcohols by conventional means such as distillation, is not practical inasmuch as the unstable rhodium-amine complex decomposes in a distillation apparatus, thus resulting in the loss of the rhodium by plating or precipitation on the surfaces of the processing equipment.

Inasmuch as a particular advantage of utilizing a one-step synthesis of alcohol lies not only in a lower process cost and capital cost, when compared with the conventional Oxo process to produce aldehydes or alcohols, but also results in a higher yield of the desired products. This is particularly advantageous inasmuch as a loss of aldehydes which easily takes place during distillation via their condensation in a still does not occur in this process.

It is, therefore, an object of this invention to provide a process for the recovery of catalysts which have been used in a process for the production of alcohol.

A further object of this invention is found in a process for the recovery of precious metal catalysts such as rhodium complex catalyst in approximately quantitative amounts from hydroformylation reaction products.

In one aspect an embodiment of this invention resides in a process for the recovery of a metallic catalyst utilized in a hydroformylation reaction in which an olefinic hydrocarbon is treated with carbon monoxide and hydrogen at hydroformylation conditions in the presence of a Group VIII metal catalyst and an amine modifier to form a hydroformylation product, which comprises contacting said hydroformylation product with a ligand capable of forming a soluble complex with Group VIII metal catalyst at contacting conditions, separating said soluble complex from said hydroformylation product, and recovering said complex.

A specific embodiment of this invention is found in a process for the recovery of a metallic catalyst comprising hexarhodiumhexacarbonyl which has been used in a hydroformylation reaction in which hendecene is treated with carbon monoxide and hydrogen at a temperature in the range of from about 50° to about 250° C. and a pressure in the range of from about 50 to about 300 atmospheres in the presence of said catalyst, which comprises contacting the resultant dodecanol with triphenylphosphine at a temperature in the range of from about 20° to about 300° C. and a pressure in the range of from about atmospheric to about 200 atmospheres, separating the resultant soluble complex from said dodecanol, and recovering said complex.

Other objects and embodiments will be found in the following further detailed description of the present invention.

As hereinbefore set forth, the present invention is concerned with a process for the recovery of catalysts which have been utilized in the synthesis of alcohols by means of a hydroformylation reaction involving the treatment of olefinic hydrocarbons with carbon monoxide and hydrogen. The synthesis of the alcohols is effected by reacting these olefinic hydrocarbons with carbon monoxide and hydrogen in the presence of a catalyst comprising a complex containing a Group VIII metal and a promoter or modifier comprising an amine compound, and preferably a tertiary amine. The reaction conditions which are employed to synthesize the alcohol will include a temperature of from about 50° to about 250° C. and a pressure in the range of from about 50 to about 300 atmospheres. In the preferred embodiment of the invention the pressures which are employed to effect the desired result will be the autogenous pressures resulting from the presence of hydrogen and carbon monoxide in the reaction mixture. However, it is also contemplated within the scope of this invention that the pressures resulting from the use of hydrogen and carbon monoxide will comprise only a partial operating pressure, the remainder being provided for by the introduction of a substantially inert gas such as nitrogen, helium, argon, etc., into the reaction vessel. In addition, other reaction conditions which are present during the synthesis of the alcohol will include a mole ratio of hydrogen to carbon monoxide in the range of from about 0.5:1 to about 5:1 moles of hydrogen per mole of carbon monoxide, a mole ratio of olefin to catalyst in the range of from about 500:1 to about 2000:1 moles of olefin per mole of catalyst and a mole ratio of tertiary amine modifier to catalyst in the range of from about 50:1 to about 300:1 moles of amine per mole of catalyst.

Examples of olefinic hydrocarbons which may be employed to effect the process of this invention will include straight and branched chain olefins containing from 2 to about 30 carbon atoms such as propylene, butene-1, butene-2, isobutylene, pentene-1, pentene-2, isopentene, as well as the isomeric hexenes, heptenes, octenes, nonenes, decenes, undecenes, dodecenes, tridecenes, tetradecenes, pentadecenes, hexadecenes, heptadecenes, octadecenes, nonadecenes, eicosenes, henicosenes, docosenes, tricosenes, tetracosenes, pentacosenes, hexacosenes, heptacosenes, octacosenes, nonacosenes, triacontenes, etc.; product mixtures produced by the dehydrogenation of $C_{11}$ to $C_{14}$ n-paraffins containing $C_{11}$ to $C_{14}$ n-olefins as well as unconverted $C_{11}$ to $C_{14}$ n-paraffins or olefin fractions of paraffin dehydrogention processes; olefin fractions of cracking processes; ethylenically unsaturated compounds such as styrene, allyl alcohol, methyl vinyl ketone, and cyclohexene.

The reaction between the olefinic hydrocarbon of the type hereinbefore set forth, carbon monoxide and hydrogen is effected in the presence of a Group VIII metal complex catalyst which may be organometallic in nature or which may comprise a salt which is converted to the complex catalyst during the process under the reaction conditions employed. Specific examples of these Group VIII metal catalysts will include rhodium nitrate, rhodium chloride, rhodium bromide, rhodium iodide, rhodium fluoride, chlorodicarbonylrhodium dimer, rhodium carbonyl, chlorobis(ethylene)rhodium dimer, hexarhodiumhexadecacarbonyl, tetrarhodiumdodecacarbonyl, rhodium acetate, rhodium acetylacetonate, ruthenium nitrate, ruthenium chloride, ruthenium bromide, ruthenium iodide, ruthenium carbonyl, ruthenium acetate, chlorodicarbonylruthenium dimer, chlorobis(ethylene)ruthenium dimer, cobalt nitrate, cobalt chloride, cobalt bromide, cobalt iodide, cobalt acetate, cobalt acetylacetonate, hexacobalthexadecacarbonyl. The modifier which is utilized to selectively form alcohols will comprise a tertiary monoamine, said tertiary monoamine including alkyl amines, aryl amines, heterocyclic amines, cycloalkyl amines, etc., such as trimethylamine, triethylamine, tripropylamine, the isomeric tributylamines, tripentylamines, trihexylamines, triheptylamines, trioctylamines, trinonylamines, tridecylamines, dimethylethylamine, dimethylpropylamine, dimethylbutylamine, dimethyldodecylamine, triphenylamine, tribenzylamine, tri-o-tolylamine, tri-m-tolylamine, tri-p-tolylamine, tricyclopentylamine, tricyclohexylamine, N-methylpyridine, N-methylpyran, N-ethylpyridine, N-ethylpyran, etc. It is to be understood that the aforementioned olefinic hydrocarbons, Group VIII metals and tertiary amines are only representative of the class of compounds which may be employed and that the present invention is not necessarily limited thereto.

After synthesizing the alcohol utilizing the desired modifiers, catalysts and operating conditions, the product is recovered and the Group VIII metal complex catalyst is separated therefrom by extracting the catalyst from the alcohol utilizing a treatment involving an aqueous ammonium hydroxide solution. This step of the process is effected by treating conditions which will include a temperature in the range of from about ambient (20°–25° C.) to about 100° C. and a pressure in the range of from about atmospheric to about 50 atmospheres. In the event that superatmospheric pressures are employed in the treating step, the pressures are afforded by the introduction of a substantially inert gas such as nitrogen into the reaction vessel. After allowing the treatment to take place during a period which may range from about 0.1 up to about 20 hours or more in duration, the aqueous ammonium hydroxide solution which contains from about 5 to about 50% by weight of ammonia is stripped of said ammonia by treatment with a stripping agent. The stripping of the ammonia is accomplished by treatment with an agent which may comprise carbon monoxide or a carbon monoxide-containing gas such as a mixture of carbon monoxide and hydrogen, carbon monoxide and nitrogen, carbon monoxide and helium, carbon monoxide and argon, etc. The stripping effected at temperatures which may range from about ambient up to about 150° C. and the pressuures ranging from about 0.1 to about 5 atmospheres.

Following the stripping of the ammonia a portion of the water in the aqueous solution is also removed by conventional means such as distillation, following which the remainder of the solution containing the Group VIII metal complex catalyst may be recycled to the hydroformylation zone for use as a catalyst in the hydroformylation reaction.

As hereinbefore set forth the hydroformylation product comprising an alcohol will, after the extraction step, still contain a trace amount of the metal catalyst usually less than about 1 ppm which is difficult to extract. Therefore, it is necessary to separate this trace amount of the metal still contained in the alcohol product without losing the catalyst via precipitation of the species or of the species plating out in a distillation apparatus.

The separation of the trace amount of the metal is accomplished by treating the product alcohol with a biphyllic ligand which is capable of forming a soluble and stable complex toward distillation with the Group VIII metal catalyst. In the process of the present invention the preferred ligands will include compounds containing arsenic, nitrogen, oxygen, phosphorous, selenium, sulfur, tellurium, antimony, germanium, or tin. Some specific examples of these compounds will include arsenic containing compounds such as bis(1,2-diphenylarsino)ethane, methyldiphenylarsine, o-phenylbis(dimethylarsine), 1-diphenylphosphino-2-diphenylarsinoethane, ethyldiphenylarsine, propyldiphenylarsine, phenylenebis(diethylarsine), phenylenebis(dipropylarsine), 1-diphenylphosphino-2-diphenylarsinopropane, etc.; nitrogen containing compounds such as hydrogen cyanide, 2,2'-bipyridine, dimethylglyoxime, 1,5,8,12-tetraazododecane, porphyrins, etc.; oxygen containing compounds such as acetylacetonate, crown ethers, etc.; phosphorous containing compound such as bis(1,2-diphenylphosphino)ethane, bis(1,3-diphenylphosphino)propane, bis(1,4-diphenylphosphino)butane, bis(diphenylphosphino)methane, 4-ethyl-2,6,7-trioxa-1-phosphobicyclo[2.2.2]octane, trimethylphosphite, triethylphosphite, tripropylphosphite, tri-n-butylphosphite, triphenylphosphine, triphenylphosphine oxide, triphenylphosphine sulfite, triphenylphosphite, etc.; sulfur containing compounds such as 1,2-dimercapto-4-methylbenzene, sodium cis-1,2-dicyanoethylene-1,2-dithiolate, etc.; selenium containing compounds such as phenylphenylthioselenide, 1,2-diselenolane, dimethyltriselenide, diethyltriselenide, etc.; tellurium containing compounds such as tetraphenyltelluride, methyldiphenyltellurium iodide, ethyldiphenyltellurium iodide, triphenyltellurium iodide, etc.; antimony containing compounds such as trimethylstibine, triethylstibine, tripropylstibine, tri-n-butylstibine, triphenylstibine, tetraphenylstibonium iodide, etc.; germanium containing compounds such as diphenylgermanium iodide, triphenylgermanium iodide, trimethylgermanium chloride, triethylgermanium chloride, tri-n-propylgermanium chloride, etc.; tin containing compounds such as dimethylisobutyltin bromide, diethylisobutyltin bromide, trimethyltin chloride, triethyltin chloride, tripropyltin chloride, diamylmethyltin iodide, etc. It is to be understood that the aforementioned biphyllic ligands are only representative of the class of compounds which may be employed, and that the present invention is not necessarily limited thereto.

The treatment of the alcohol product with the biphyllic ligand is effected by contacting the alcohol in an appropriate apparatus. In addition, if so desired, the mixture of ligand and product may undergo treatment in the presence of carbon monoxide or a carbon monoxide containing gas at an elevated temperature and pressure in order to facilitate the formation of the complex with the ligand. However, it is understood that the presence of the gas of the type hereinbefore set forth at an elevated temperature is optional and that the formation of the soluble complex may be effected at atmospheric temperature and pressure in the absence of carbon monoxide or a carbon monoxide containing gas.

The process of this invention may be effected in any suitable manner and may comprise either a batch or continuous type operation. For example, when a batch type operation is used, a quantity of the olefin which is to be hydroformylated is charged to a pressure resistant apparatus such as an autoclave of the rotating, mixing or stirring type, said apparatus containing the Group VIII metal complex catalyst and the tertiary amine which acts as a modifier. The autoclave is sealed and carbon monoxide and hydrogen pressured in until the desired operating pressure has been attained. Thereafter the reactor is heated to the desired operating temperature and maintained thereat for a predetermined period of time which may range from about 0.5 up to about 10 hours or more in duration. Following the completion of the desired reaction period, heating is discontinued and after the apparatus has returned to room temperature the excess pressure is discharged and the reaction mixture is recovered therefrom. The reaction mixture is then charged to a second apparatus which may also be of the pressure resistant type, if so desired, and the reaction mixture is contacted with an aqueous ammonium hydroxide solution at reaction conditions hereinbefore set forth in greater detail. Upon completion of the extraction or treatment period the aqueous ammonium hydroxide solution containing the extracted Group VIII metal complex catalyst is separated from the organic phase which comprises the product alcohol and the amine modifier. The aqueous ammonium hydroxide solution containing the extracted Group VIII complex catalyst is stripped by treatment with carbon monoxide. The stripping operation is also effected at reaction conditions hereinbefore set forth for a period of time which may range from about 0.5 up to about 10 hours or more in duration. Following the stripping of the aqueous ammonium hydroxide solution the solution is then stripped or distilled of a portion of the water and the remaining aqueous solution of Group VIII metal complex catalyst is recycled back to the hydroformylation zone for use therein. The product alcohol containing a trace amount of catalyst is then contacted in a reaction zone with a ligand of the type hereinbefore set forth and, if so desired, carbon monoxide or a carbon monoxide containing gas at a temperature in the range of from about 20° to about 300° C. and a pressure in the range of from about atmospheric to about 200 atmospheres. Following this, the product alcohol which contains the soluble complex catalyst and the amine modifier may then be subjected to distillation zone wherein the amine modifier and the catalyst are separated from the product alcohol, the latter then being sent to storage.

It is also contemplated within the scope of this invention that the process of the present invention may be effected in a continuous manner of operation. When such a type of operation is employed the starting material comprising olefinic hydrocarbon is continuously charged to a reaction zone which is maintained at the proper operating conditions of temperature and pressure and which contains a Group VIII metal complex catalyst as well as a tertiary amine modifier. The desired operating pressures are attained by utilizing the autogenous pressures afforded by the carbon monoxide and hydrogen which are required for the hydroformylation reaction. After passage through the reaction zone for a predetermined period of time the reactor effluent is continuously withdrawn and passed to an extraction zone wherein said effluent is contacted or treated with an aqueous ammonium hydroxide solution also continuously charged to said zone. After passage through the extraction zone the aqueous layer comprising an ammonium hydroxide solution containing the catalyst is separated from the organic phase which comprises the product alcohol which contains a small portion of catalyst and the amine buffer. The aqueous phase is continuously charged to a stripping zone wherein it is contacted with carbon monoxide or a carbon monoxide containing gas at stripping conditions whereby any free ammonia present in the ammonium hydroxide solution is stripped therefrom. The stripped solution containing the catalyst is then continuously charged to a distillation zone whereby a portion of the water is stripped therefrom and the remaining solution is recycled to the hydroformylation zone for use as a catalyst therein. The product alcohol, after separation from the aqueous layer, is continuously charged to a contact zone wherein it is contacted with a biphyllic ligand under, if so desired, an implied pressure of carbon monoxide and a carbon monoxide containing gas, said contact zone being maintained at the proper operating conditions of temperature and pressure. After passage through this contact zone the mixture is continuously charged to a distillation zone or a series of distillation zones whereby the amine modifier is separated and recycled to the hydroformylation zone while the product alcohol is separated from the soluble complex catalyst and removed to storage while the catalyst complex is recovered for further use.

BRIEF DESCRIPTION OF THE DRAWING

The present invention will be further illustrated with reference to the accompanying drawing which sets forth a flow diagram of one embodiment of the process of this invention. It it to be understood that various valves, pumps, etc., have been eliminated as not being essential to the complete understanding of the invention. However, the utilization of these as well as other similar appurtenances will become obvious as the drawing is described.

Referring now to the drawing, an olefinic hydrocarbon which is to be hydroformylated is charged to reaction zone 1 through lines 2 and 3 along with a Group VIII metal complex catalyst of the type hereinbefore set forth, amine modifier and start-up carbon monoxide and hydrogen. In zone 1 the olefinic hydrocarbon is subjected to hydroformylation reaction at conditions hereinbefore set forth. After passage through the reaction zone for a predetermined period of time the hydroformylation product along with the catalyst and any unreacted carbon monoxide and hydrogen is withdrawn from zone 1 through line 4 and passed to separation zone 5. In separation zone 5 the aforesaid unreacted carbon monoxide and hydrogen is separated from the liquid product and withdrawn through line 6 for recycle back to reaction zone 1 through lines 2 and 3.

The liquid reaction product is withdrawn from separation zone 5 through line 7 and passed to extraction zone 8 wherein it is contacted with an aqueous ammonium hydroxide solution which is charged to zone 8 through line 9. If so desired, the organic liquid product and the aqueous liquid product may be withdrawn from separation zone 5 and passed to extraction zone 8 through separate lines. In extraction zone 8 the Group VIII metal complex catalyst which has become entrained or dissolved in the organic phase is extracted therefrom. The aqueous ammonium hydroxide solution containing the aforesaid catalyst is withdrawn from extraction zone 8 through line 10 and passed to stripping zone 11. In stripping zone 11 the ammonia is stripped from the aqueous ammonium hydroxide solution by contact with carbon monoxide or a carbon monoxide containing gas which is charged to zone 11 through line 12. In addition, a portion of the water is also stripped from the solution in stripping zone 11 by conventional means and the resulting Group VIII metal complex catalyst is recycled to reaction zone 1 through line 3. The ammonia and water which have been stripped in stripping zone 11 are withdrawn through line 13 and recycled to extraction zone 8 through lines 9 and 13.

The liquid product which contains a trace amount of the catalyst along with the amine modifier is withdrawn from extraction zone 8 through line 14 and passed to treatment zone 15. In treatment zone 15 the product is contacted with a biphyllic ligand of the type hereinbefore set forth which is charged to zone 15 through line 16. In addition, if so desired, the treatment of the product with the ligand may be effected in the presence of carbon monoxide or a carbon monoxide containing gas such as a mixture of carbon monoxide and hydrogen which is charged to treatment zone 15 through line 17. After treatment in zone 15 at reaction conditions which may include a temperature in the range of from about 20° to about 300° C. and a pressure in the range of from about atmospheric to about 200 atmospheres, the product alcohol and the solubilized complex catalyst and amine modifier are withdrawn through line 18 and passed to distillation zone 19. In distillation zone 19 the amine modifier is separated from the product alcohol and withdrawn through line 20 for recycle back to reaction zone 1. The product alcohol is withdrawn from zone 19 through line 21 and passed to a second distillation zone 22. In this zone the product alcohol is separated from any heavies which will cause the catalyst and withdrawn through line 23 for storage while the heavies containing the catalyst are withdrawn through line 24 for recovery of the catalyst by means not shown in the drawing.

The following examples are given to illustrate the process of the present invention. However, it is to be understood that these examples are given merely for purposes of illustration and that the present invention is not necessarily limited thereto.

EXAMPLE I

An olefin charge comprising 650 grams of a blend of n-hendecene with smaller amounts of aromatic and paraffinic impurities was charged to a rotating autoclave along with 0.62 grams of hexarhodiumhexadecacarbonyl and 110 grams of an amine modifier comprising dimethyldodecylamine. The autoclave was sealed and 210 atmospheres of a 1:1 blend of carbon monoxide and hydrogen was charged thereto at room temperature. The autoclave was then heated to a temperature of 150° C. and maintained thereat for a period of 8 hours, the pressure during this time dropping to 70 atmospheres. At the end of the 8 hour period heating was discontinued and after the autoclave was allowed to return to room temperature the excess pressure was discharged and the reaction mixture was recovered therefrom. The deep red hydroformylation product was analyzed by standard gas-liquid chromatographic techniques to determine that there had been a 100% conversion of the hendecene with a mole percent selectivity of greater than 95% to dodecanol.

EXAMPLE II

The product, in an amount of 850 grams, which contained a rhodium concentration of about 175 ppm was treated with 850 grams of an aqueous ammonium hydroxide solution containing 30% by weight of ammonia. The treatment was effected at room temperature for a period of 3.5 hours. After treatment with the aqueous ammonium hydroxide solution the dark green aqueous phase was separated from the organic phase in a separatory funnel under a nitrogen blanket. Analysis of the raffinate or organic phase disclosed that the raffinate contained 10.5 ppm of rhodium.

EXAMPLE III

To determine the efficiency for the removal of rhodium from the raffinate a series of experiments were performed. In the first experiment 240 grams of the raffinate was placed in a flask which was then heated to a temperature of 250° C. under a blanket of nitrogen. The distillation of the raffinate was allowed to proceed for a period of 1.8 hours. At the end of this time analysis showed that of the rhodium present in the alcohol product 60% precipitated, 15.4% plated on the flask, and only 24.6% was soluble.

To illustrate the efficiency of the ligand a second experiment was performed in which 231 grams of the raffinate along with 1.52 grams of triphenylphosphine was placed in a flask and distilled at a temperature of 240° C. for a period of 0.5 hours. Analysis of the product showed that 96.2% of the rhodium was recovered in soluble form while only 3.4% precipitated and 0.4% plated out. Similar results were obtained when the experiment was repeated by distilling 234 grams of raffinate and 2.0 grams of triphenylphosphine for a temperature of 250° C. for a period of 1.6 hours. Again only 2.6% of the rhodium precipitated and 0.5% plated out, the remaining 96.9% being in soluble form.

In this experiment 240 grams of the raffinate along with 1.03 grams of bis(1,2-diphenylphosphino)ethane was treated in a manner similar to that set forth in the above paragraph. Analysis determined that 1.5% of the rhodium precipitated and 0.5% plated out, the remainder being in soluble form.

I claim as my invention:

1. In a process for the recovery of trace amounts of a Group VIII metallic catalyst from a hydroformylation reaction product consisting essentially of an alcohol derived from hydroformylation of an olefinic hydrocarbon with carbon monoxide and hydrogen at hydroformylation conditions in the presence of a Group VIII metal catalyst and a monoamine modifier, the improvement which comprises, after hydroformylation, contacting at a temperature in the range of from about 20° to about 300° C. and a pressure in the range of from about 1 atmosphere to about 200 atmospheres said hydroformylation reaction product consisting essentially of an alcohol with a biphyllic ligand compound selected from the group consisting of arsenic, nitrogen, oxygen, phosphorous, sulfur, tellurium, antimony, germanium and tin compounds capable of forming a soluble and stable complex with said Group VIII metallic catalyst to separate and recover said trace amounts of Group VIII metallic catalyst.

2. The process as set forth in claim 1 in which hydroformylation conditions include a temperature in the range of from about 50° to about 250° C. and a pressure in the range of from about 50 to about 300 atmospheres.

3. The process as set forth in claim 1 in which said Group VIII metal catalyst comprises a rhodium complex catalyst.

4. The process as set forth in claim 3 in which said rhodium complex catalyst is chlorodicarbonylrhodium dimer.

5. The process as set forth in claim 4 in which said rhodium complex catalyst is hexarhodiumhexadecacarbonyl.

6. The process as set forth in claim 1 in which said biphyllic ligand capable of forming a soluble complex with a Group VIII metallic catalyst comprises triphenylphosphine.

7. The process as set forth in claim 1 in which said biphyllic ligand capable of forming a soluble complex with a Group VIII metallic catalyst comprises bis(1,2-diphenylphosphino)ethane.

8. The process as set forth in claim 1 in which said biphyllic ligand capable of forming a soluble complex with a Group VIII metallic catalyst comprises methyldiphenylarsine.

9. The process as set forth in claim 1 in which said biphyllic ligand capable of forming a soluble complex with a Group VIII metallic catalyst comprises triphenylphosphite.

10. The process as set forth in claim 1 in which said biphyllic ligand capable of forming a soluble complex with a Group VIII metallic catalyst comprises triphenylphosphine sulfide.

11. The process as set forth in claim 1 further characterized in that the contact of the hydroformylation product with said biphyllic ligand is effective in the presence of carbon monoxide or a carbon monoxide containing gas.

12. The process as set forth in claim 11 in which said carbon monoxide containing gas is a mixture of carbon monoxide and hydrogen.

13. The process as set forth in claim 1 in which said olefinic hydrocarbon contains from 2 to about 30 carbon atoms.

14. The process as set forth in claim 1 in which said olefinic hydrocarbon is hendecene and said hydroformylation product is dodecanol.

15. The process as set forth in claim 13 in which said olefinic hydrocarbon is butene and said hydroformylation product is pentanol.

16. The process as set forth in claim 13 in which said olefinic hydrocarbon is a product mixture produced in the dehydrogenation of $C_{11}$ to $C_{14}$ n-paraffins containing $C_{11}$ to $C_{14}$ n-olefins as well as unconverted $C_{11}$ to $C_{14}$ n-paraffins and said hydroformylation product is $C_{12}$ to $C_{15}$ alcohols.

* * * * *